US00PP12442P2

(12) United States Plant Patent
Johnson

(10) Patent No.: US PP12,442 P2
(45) Date of Patent: Mar. 5, 2002

(54) PETUNIA PLANT NAMED 'WHITE SPICE'

(75) Inventor: David Zane Johnson, East Bend, NC (US)

(73) Assignee: Farmstead Nursery, Inc., East Bend, NC (US)

( * ) Notice: Subject to any disclaimer, the term of this patent is extended or adjusted under 35 U.S.C. 154(b) by 0 days.

(21) Appl. No.: 09/624,466

(22) Filed: Jul. 24, 2000

(51) Int. Cl.[7] ..... A01H 5/00

(52) U.S. Cl. ..... Plt./356

(58) Field of Search ..... Plt./356

*Primary Examiner*—Bruce R. Campell
*Assistant Examiner*—Wendy C Baker
(74) *Attorney, Agent, or Firm*—C. A. Whealey

(57) ABSTRACT

A distinct cultivar of Petunia plant named 'White Spice', characterized by its uniform cascading and spreading plant habit; freely and continuous branching; numerous fragrant white-colored flowers; excellent garden performance; and tolerance to high temperatures.

1 Drawing Sheet

BACKGROUND OF THE INVENTION

The present Invention relates to a new and distinct cultivar of Petunia plant, botanically known as *Petunia×hybrida*, and hereinafter referred to by the cultivar name White Spice.

The new Petunia is a product of a planned breeding program conducted by the Inventor in East Bend, N.C. The new Petunia originated from a self-pollination made by the Inventor of the *Petunia×hybrida* cultivar Purple Wave, not patented. The new Petunia was selected from a single plant of the resulting progeny by the Inventor in June, 1998, on the basis of its white-colored flowers.

Asexual reproduction of the new cultivar by terminal cuttings taken in East Bend and Winston-Salem, N.C. has shown that the unique features of this new Petunia are stable and reproduced true to type in successive generations.

SUMMARY OF THE INVENTION

Plants of the cultivar White Spice have not been observed under all possible environmental conditions. The phenotype may vary somewhat with variations in environment such as temperature, light intensity, daylength, and fertility level without, however, any variance in genotype.

The following traits have been repeatedly observed and are determined to be the unique characteristics of 'White Spice'. These characteristics in combination distinguish 'White Spice' as a new and distinct cultivar:

1. Uniform cascading and outwardly spreading plant habit.

2. Freely and continuous branching.

3. Numerous fragrant white-colored flowers.

4. Excellent garden performance and tolerance to high temperatures.

Compared to plants of the parent cultivar, Purple Wave, plants of the new Petunia have fragrant white-colored flowers whereas flowers of 'Purple Wave' are purple-colored and not fragrant.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new Petunia.

The photograph at the top of the sheet comprises a top perspective view of typical plants of 'White Spice' (foreground) and 'Purple Wave' (background).

The photograph at the bottom of the sheet comprises a close-up view of typical flowers of 'White Spice'.

DETAILED BOTANICAL DESCRIPTION

In the following description, color references are made to The Royal Horticultural Society Colour Chart except where general terms of ordinary dictionary significance are used. Ten to twelve-week old plants grown in 15-cm containers were used for the following description. Plants were grown under conditions which closely approximate commercial production conditions in Winston-Salem, N.C.

Botanical classification: *Petunia×hybrida* cultivar White Spice.

Parentage: Self-pollination of *Petunia×hybrida* cultivar Purple Wave, not patented.

Propagation:

*Type cutting.*—Terminal vegetative cuttings.

*Time to initiate roots, summer.*—About 14 days at 29° C.

*Time to initiate roots, winter.*—About 30 days at 13° C.

*Time to develop roots, summer.*—About 30 days at 29° C.

*Time to develop roots, winter.*—About 60 days at 13° C.

*Root description.*—Numerous, thick, fibrous and well-branched.

Plant description:

*Form.*—Annual flowering plant; indeterminate; initially upright, then cascading and outwardly spreading; uniform; plants eventually becoming hemispherical to spherical in shape. Viscid and glandular pubescent. Freely basal branching with about 15 lateral branches per plant.

*Usage.*—Appropriate for hanging baskets, window boxes, patio containers and landscape applications.

*Crop time.*—About 10 to 12 weeks are required to produce finished flowering plans in 15-cm containers.

*Plant height.*—About 21 cm.

*Plant diameter.*—About 57 cm.

*Vigor.*—Moderate vigor to vigorous.

*Lateral branches.*—Length: About 31 cm. Diameter: Thick, about 3.25 cm. Internode length: About 1.75 cm. Texture: Pubescent; viscid, glandular. Color: More green and darker than 146A.

*Foliage description.*—Leaves simple, generally symmetrical and long-persisting; opposite. Quantity per lateral branch: About 26. Length: About 5.8 cm. Width: About 2.8 cm. Shape: Mostly obovate. Apex: Acute to broadly acute. Base: Attenuate. Margin: Entire. Aspect: Typically horizontal. Texture: Rough, coarse; pubescence on both surfaces; glandular, viscid. Color: Young foliage, upper surface: Darker and more green than 146A. Young foliage, lower surface: Close to 146B. Mature foliage, upper surface: Darker and more green than 146A. Mature foliage, lower surface: Close to 146B. Petiole length: About 1.1 cm. Petiole diameter: About 2.3 mm. Petiole color: Close to 146C.

Flower description:

*Flower type and habit.*—Medium-sized salverform flowers; flowers face mostly upward or outward; single, axillary. Flowers persistent. Very freely flowering, typically about 200 open flowers and flower buds per plant.

*Natural flowering season.*—Long day responsive; spring until frost in the autumn; flowering continuous.

*Flower longevity on the plant.*—About one week.

*Fragrance.*—Spicy sweet fragrance, pleasant.

*Flower size.*—Diameter: About 6.3 cm. Tube length: About 4.1 cm. Throat diameter, distal end: About 1.1 cm. Tube diameter, proximal end: About 2.5 mm.

*Flower buds* (*just before showing color*).—Length: About 2.1 cm. Diameter: About 5 mm. Shape: Elongated oblong with slightly ruffled apices. Color: 144A to 144B.

*Corolla.*—Arrangement/appearance: Single whorl of five petals, fused into flared trumpet. Petal length from throat: About 2.8 cm. Petal width: About 2.5 cm. Petal shape: Roughly spatulate. Petal apex: Acute to somewhat cuspidate. Petal margin: Entire; slightly undulate. Petal texture: Smooth, velvety; flower tube, pubescent. Color: Petal, upper surface, when opening and fully opened flower: White, 155D; occasional red purple speckles, close to 66A, random in size, shape and location. Petal, lower surface, when opening and fully opened flower: White, 155D. Flower throat (inside): White, 155D. Flower tube (outside): White, 155D. Veins, upper surface: 144A to 146A. Veins, lower surface: 144A.

*Sepals.*—Arrangement/appearance: Single whorl of five sepals, star-shaped. Length: About 1.2 cm. Width: About 3 mm. Shape: Strap-like; narrow, elongate. Apex: Rounded. Margin: Entire. Texture: Pubescence mostly on lower surface and at margins. Color, upper and lower surface: More green than 146A.

*Peduncles.*—Length: About 1.7 cm. Width: About 1 mm. Angle: About 45 to 90° to the stem dependent on stem orientation. Strength: Moderately strong; hold flowers upward or outward. Texture: Pubescent. Color: More green than 146A.

*Reproductive organs.*—Stamens: Quantity: About five. Anther shape: Somewhat ovoid. Anther length: About 2 mm. Anther color: White, 155D. Filament color: White, 155D. Pollen amount: Moderate. Pollen color: Creamy white. Pistils: Quantity: One. Pistil length: About 1.8 cm. Stigma shape: Oblong; slightly bi-lobed. Stigma color: Close to 144A. Style color: 144D. Ovary color: 144A.

*Seed.*—Seed production has not been observed.

Disease resistance: Plants of the new Petunia have not been noted to be unusually resistant or susceptible to pathogens common to Petunia.

Weather tolerance: Plants of the new Petunia have been observed to be tolerant to rain and wind and very tolerant to temperatures above 35° C.

It is claimed:

1. A new and distinct cultivar of Petunia plant named 'White Spice', as illustrated and described.

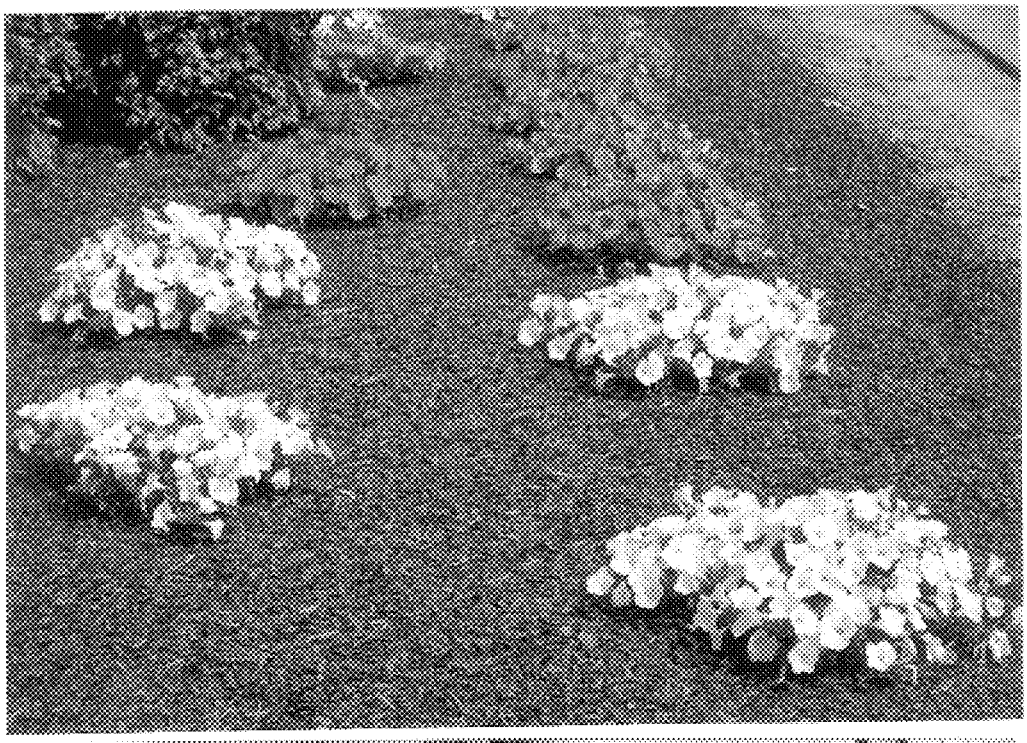
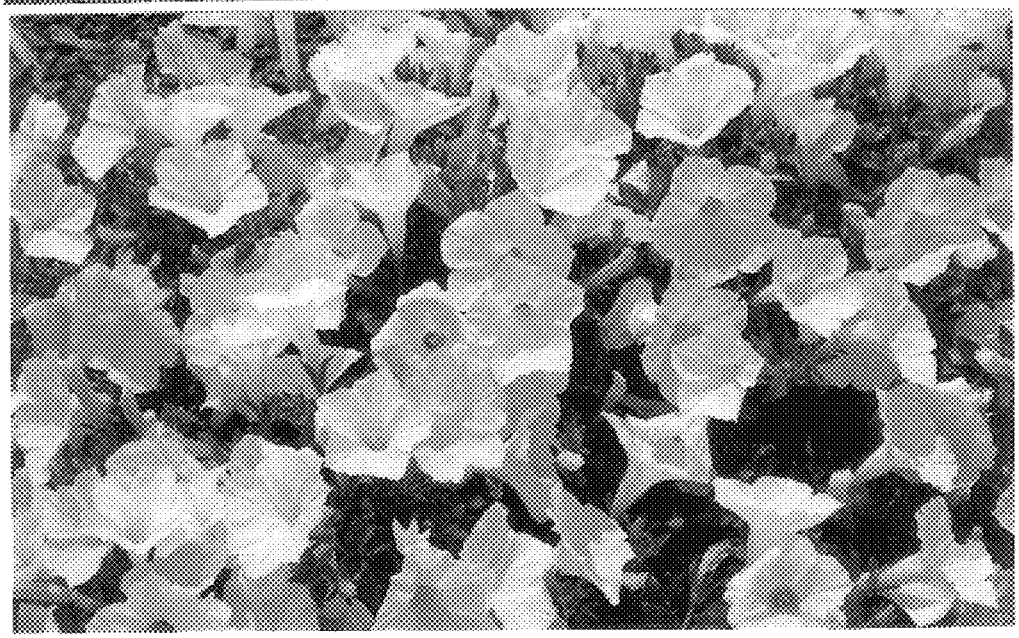

* * * * *